United States Patent [19]
Johnstone et al.

[11] Patent Number: 5,473,101
[45] Date of Patent: Dec. 5, 1995

[54] OXIDATION OF ALKYLAROMATICS

[75] Inventors: Alexander Johnstone, Little Neston; Kenneth T. Rowbottom, Woolston; William R. Sanderson, Penketh, all of United Kingdom; Martin Jeff, Houston, Tex.; Miranda Service, Latchford, United Kingdom

[73] Assignee: Solvay Interox Limited, Warrington, England

[21] Appl. No.: 167,903

[22] PCT Filed: Jun. 16, 1992

[86] PCT No.: PCT/GB92/01076

§ 371 Date: Apr. 13, 1994

§ 102(e) Date: Apr. 13, 1994

[87] PCT Pub. No.: WO93/00319

PCT Pub. Date: Jan. 7, 1993

[30] Foreign Application Priority Data

Jun. 21, 1991 [GB] United Kingdom .................... 9113476

[51] Int. Cl.$^6$ ................................................ C07C 51/16
[52] U.S. Cl. ............................................. 562/416; 562/409
[58] Field of Search ...................... 562/409, 416

[56] References Cited

U.S. PATENT DOCUMENTS 3,914,295  10/1975  Rosenthal et al. ................ 260/524 M
4,007,256   2/1977  Kim et al. ............................ 562/409

FOREIGN PATENT DOCUMENTS 1168887   4/1964   Germany .
1275047   8/1968   Germany .
2759027   7/1978   Germany .
7028973   9/1970   Japan .
 467060   7/1975   U.S.S.R. .
1198261   7/1970   United Kingdom .
2182928   5/1987   United Kingdom .

OTHER PUBLICATIONS

J. Dakka et al.; Mar. 29, 1988, p. 756; "Hydrobromic Acid Catalzed Oxidation of Benzyl Alcohols by Hydrogen Peroxide"; Bulletin De LaSociete Chimique De France, No. 4, 1988, Paris.

Primary Examiner—Paul J. Killos
Attorney, Agent, or Firm—Larson and Taylor

[57] ABSTRACT

A process for the controlled oxidation of alkyaromatic compounds comprises reacting said compounds with an oxidising system, comprising cobalt (II) ions, bromide ions, and hydrogen peroxide, in the presence of an appropriate protic solvent.

The process is particularly useful in the selective oxidation of poly(alkyl)aromatic compounds.

32 Claims, No Drawings

OXIDATION OF ALKYLAROMATICS

This Application is a 371 of PCT/GB92/01076 filed 16 Jun. 1992.

This invention concerns a process for the oxidation of alkylaromatic compounds using an oxidising system comprising cobalt salts and hydrogen peroxide.

The oxidation of alkylaromatic compounds using oxidising systems comprising cobalt salts is known in the art.

U.S. Pat. Nos. 3,665,030 and 3,969,405 disclose that alkylaromatic compounds may be oxidised to aromatic carboxylic acids using an oxidation system comprising a cobalt acetate catalyst, acid activator and molecular oxygen oxidant. The reaction is not commercially satisfactory for the preparation of carboxylic acids since the reaction times required to obtain high conversion rates are too long. Furthermore, the reaction tends not to be selective in the preparation of monocarboxylic acid aromatics from poly-(alkyl)aromatics (see U.S. Pat. No. 3,665,030, particularly Example XXVI and Example XXXVII, and U.S. Pat. No. 3,969,405, particularly Examples XXXVII to XLIV).

U.S. Pat. Nos. 4,323,692 and 4,401,828 disclose that phenoxytoluenes may be oxidised to phenoxybenzoic acids in the presence of from 0.001 to 0.5 moles of a cobalt (II) salt catalyst per mole of phenoxytoluene, from 1 to 3 equivalents of bromide ion per mole of cobalt (II) salt, from 0.5 to 1 mole of hydrogen peroxide activator per mole of cobalt (II) salt and the introduction of gaseous oxygen oxidant.

U.S. Pat. No. 3,519,684 discloses a process for producing aromatic dicarboxylic acids from di(alkyl)aromatic compounds using an oxidising system comprising a cobalt salt catalyst, peracetic acid activator and the introduction of gaseous oxygen oxidant.

It is an object of the present invention to provide a process for the oxidation of alkylaromatic compounds, which process does not essentially require the introduction of gaseous oxygen.

It is a further object of the present invention to provide a process for the oxidation of alkylaromatic compounds which process may achieve high conversion and high yields of oxidised products by a one-pot reaction.

It is yet a further object of the present invention to provide a process for the selective oxidation of poly(alkyl)aromatic compounds to form aromatic carboxylic acid compounds, which process does not essentially require the introduction of gaseous oxygen as oxidant.

In accordance with the present invention, there is provided a process for oxidising an alkylaromatic compound, which process comprises reacting said alkylaromatic compound with an oxidising system comprising from at least 0.01 moles of cobalt (III) ions per mole of alkylaromatic compound, from at least 0.01 moles of bromide ions per mole of alkylaromatic compound, and from more than 0.5 mole, preferably more than 1 mole, of hydrogen peroxide per mole of alkylaromatic compound, in the presence of an appropriate protic solvent selected from the group consisting of the carboxylic acids having from one to five carbon atoms, said alkylaromatic compound having at least one alkyl substituent which is not tertiary at the carbon positioned alpha to the aromatic ring.

The preferred protic solvents are acetic acid, propionic acid and butyric acid, the most preferred being acetic acid. The protic solvent may be present in any reasonable amount but is preferably present in an amount of at least 3 times the weight of the alkylaromatic compound and preferably no more than 15 times, such as from 3 to 12 times, the weight of the alkylaromatic compound. When the alkylaromatic compound is a poly(alkyl) aromatic compound, the preferred amount of protic solvent used is from 4 to 10 times the weight of the poly(alkyl)aromatic compound. When the alkylaromatic compound is a mono-alkylaromatic compound, the preferred amount of protic solvent used is from 8 to 12 times the weight of the mono-alkylaromatic compound.

In the process of the present invention, the cobalt (III) ions are preferably sourced from an in-situ oxidation of cobalt (II) ions. The cobalt (II) ions may be sourced from any appropriate cobalt (II) salt, such as cobalt (II) acetate, cobalt (II) propionate, cobalt (II) naphthenate and cobalt (II) bromide. Cobalt (II) acetate is preferred.

The cobalt (III) ions are preferably present in the oxidising system in an amount of from about 0.01 to about 0.15 moles cobalt (III) ions per mole of alkylaromatic compound. Preferably, when the alkyaromatic compound is a poly(alkyl)aromatic compound, the amount of cobalt (III) ions required is about 0.03 to about 0.1 moles of cobalt (III) ions per mole of poly(alkyl)aromatic compound. Preferably, when the alkylaromatic compound is a mono-alkylaromatic compound, the amount of cobalt (III) ions required is from about 0.02 to about 0.12 moles, more preferably from about 0.06 to about 0.12 moles, per mole of mono-alkylaromatic compound The bromide ions ($Br^-$), which are preferably present in the oxidising system in an amount of from about 0.01 to about 0.20 moles $Br^-$ per mole of alkylaromatic compound, are preferably sourced from bromine, hydrogen bromide or any appropriate bromide salt, such as ammonium bromide, cobalt (II) bromide, sodium bromide or potassium bromide. Sodium bromide is preferred. When the alkylaromatic compound is a poly(alkyl)aromatic compound, the preferred bromide ion content is from about 0.04 to 0.2 moles, more preferably 0.04 to 0.15 moles, per mole of poly(alkyl) aromatic compound, whereas the preferred amount of bromide ions present when the alkylaromatic compound is a mono-alkylaromatic compound is from about 0.02 to 0.2 moles, more preferably 0.06 to 0.2 moles, yet more preferably 0.06 to 0.16 moles, per mole of mono-alkylaromatic compound.

Hydrogen peroxide is present in the present invention in an amount of more than 0.5 mole hydrogen peroxide per mole of alkylaromatic compound. Preferably, from about 1 to about 10 moles, more preferably from about 2 to about 10 moles, of hydrogen peroxide are present per mole of alkylaromatic compound to be oxidised. Even more preferably from about 3 to about 10 moles and most preferably from about 4 to about 8 moles of hydrogen peroxide are used per mole of alkylaromatic compound.

The hydrogen peroxide is preferably added as an aqueous solution, which solution desirably has a strength of at least 25% peroxide. Preferably the solution is not stronger than 85% peroxide. The preferred solution has a strength of from about 35% to about 70% peroxide.

The alkylaromatic compounds which are oxidised most satisfactorily by the process of the present invention are those which comprise at least one alkyl, preferably a ($C_1$–$C_6$)alkyl, substituent having at least one hydrogen atom at the alpha position relative to the aromatic ring. Although higher alkyl substituents may be oxidised by the process of the present invention, such as those having up to 30 carbon atoms, ($C_1$–$C_6$)alkyl substituents are preferred. From the preferred group of substituents, straight chain ($C_1$–$C_6$)alkyl substituents and branched chain alkyl substituents having less than 5 carbons are most preferred. Typical alkylaromatic compounds which may be oxidised by the present invention include mono-, di- or tri-alkylbenzenes, such as toluene, ethylbenzene, p-t-butyltoluene, cumene, o-, m- or p-xylenes, o-, m-, p-diethylbenzenes, tri-methylbenzenes, e.g. mesitylene, and polynuclear alkylaromatic compounds such as the mono-, di- and tri-alkyl naphthalenes, e.g. methyl naphthalenes, ethyl naphthalenes and dimethylnaphthalenes.

The alkyl substituent or substituents of the alkylaromatic compounds may be any substituted alkyl which may be oxidised to an alcohol, a ketone or carboxylic acid as may be appropriate. Such substituted alkyls commonly have at least one hydrogen atom or hydroxy group at the alpha position relative to the aromatic ring. Alkyls substituted with at least one phenyl-, hydroxy-, halo- or oxy- substituent are typical of the substituted-alkylaromatic compounds which may be oxidised by the process of the present invention. For example, when the alkyl- substituent is methyl-, the methyl- may be a mono- or di-substituted methyl- of the formulae $CHR^1R^2$— or $C(OH)R^1R^2$— where $R^1$ and $R^2$ are independently selected from the group consisting of H-, substituted or unsubstituted phenyl-, —OH and hal- (halis F-, Ci-, Br- or I-), or $R^1$ and $R^2$ together are =O (oxy) i.e. an aidehyde. Typical substituted-alkylaromatic compounds are diphenylmethane and diphenylethane.

For the avoidance of doubt, reference herein to the alkyl substituent not being tertiary at the carbon positioned alpha to the aromatic ring indicates that the substituent is a methyl group, or is primary or secondary at the alpha carbon, although the alkyl substituent may contain a tertiary alkyl group elsewhere.

The alkylaromatic compounds may also be substituted on the aromatic by one or more substituents such as fluoro, chloro, bromo, iodo, nitro, or oxygenated substituents such as acyl, alkoxy, carboxyl, phenoxy and 1-acyloxyalkyl. Typical of such substituted alkylaromatic compounds are p-chlorotoluene, p-bromomethylbenzene, m-nitrotoluene, o-acetyltoluene, 4-methoxyethylbenzene, p-toluic acid, 4-methyl-1-naphthoic acid, 3-(2-chloro-4-trifluoromethylphenoxy)toluene, 4,4'-dichlorodiphenylmethane and 2,4-dichloro-diphenylmethane.

The process of the present invention is preferably effected at about atmospheric pressure, at a preferred temperature of at least 40° C. Preferably, the process is effected at a temperature of at least 60° C. The maximum temperature of the process at atmospheric pressure is determined by the reflux temperature of the mixture, which is usually about 100° C.

The overall reaction time of the process is unlikely to be less than 15 minutes and is typically run for between about 1 and 5 hours, while longer than 8 hours is very unusual. The reaction times of the processes of the present invention will typically be substantially less than the times accorded to the cobalt catalysed processes exemplified in U.S. Pat. Nos. 3,969,405 and 3,665,030, thereby demonstrating the commercial advantage of the present invention.

The cobalt and bromide catalyst for the reaction may be recovered on completion of the desired reaction, and may be recycled, so as to improve the costs and reduce the environmental impact of the process.

It has been surprisingly found that the process of the present invention gives preferential oxidation of poly(alkyl)aromatic compounds. For example, it has been found that the controlled oxidation process when applied to a poly-(alkyl)aromatic compound will selectively oxidise only one alkyl group through to the carboxylic acid before a second alkyl group is attacked to any significant degree. This is an extremely advantageous aspect of the present invention since the known processes of U.S. Pat. No. 3,969,405 do not demonstrate such selectivity.

The process of the present invention may be performed to produce alcohols, aldehydes, ketones or acids of the alkylaromatics, and is therefore very flexible. In some instances, for the production of aldehydes for example, it may be necessary for the process to be carried out under an inert atmosphere, such as nitrogen or argon, to prevent the reaction completing oxidation to the acid, though in other instances it may be found that the reaction stops at the aldehyde stage without rapidly progressing to the completely oxidised acid stage. On the other hand, where a mixture of aldehyde and acid is formed, it would be possible to force the reaction to complete oxidation by the use of a second oxidant, such as air, peracetic acid or sodium perborate.

The process according to the present invention may also be operated under forcing conditions so that the oxidation proceeds with reduced selectivity if the products of such a non-selective process are particularly desired. This may be the case where the substrate is a poly(alkyl) aromatic and it is desired to oxidise a plurality of the alkyl substituents in one reaction. Typically, such forcing conditions would comprise a combination of a temperature in the range of from about 80° C. to about 100° C., use of a hydrogen peroxide solution comprising greater than about 65% $H_2O_2$ by weight.

The invention will now be further described with reference to the following examples:

EXAMPLE I

This example demonstrates the oxidation of toluene by the process of the present invention.

Cobalt (II) acetate tetrahydrate (lg, 0.004 moles), sodium bromide (lg, 0.01 moles), toluene (0.054 moles) and acetic acid (55 g) were charged to a vessel fitted with an overhead paddle stirrer, thermometer and condenser and heated to 80° C. Hydrogen peroxide (40%, 0.44 moles) was added dropwise down the condenser over 2 hours, during which time the reaction mixture changed colour from dark blue to pink. The reaction was continued for a further two hours when it was stopped and the reaction mixture analysed by HPLC. The analysis revealed that 90.6% of the toluene had been consumed, yielding products including benzaldehyde (29.0% yield) and benzoic acid (55.6% yield).

EXAMPLE II

This is a comparative example demonstrating the oxidation of toluene by the prior art process described in U.S. Pat. No. 3,969,405.

The procedure of Example I was repeated, but this time no hydrogen peroxide was used. Instead, the reaction mixture was stirred vigorously, thereby ensuring full exposure of the reaction mixture to molecular oxygen (air), over the complete four hour period. The final reaction mixture was analysed by HPLC and it was revealed that 37.6% of the toluene had been consumed, yielding products including benzaldehyde (2.37% yield) and benzoic acid (4.33% yield).

A comparison of the results from Example I with the results from Example II clearly demonstrates the superior performance of the oxidation process of the present invention.

EXAMPLE III

The procedure of Example I was repeated, but this time cobalt (II) acetate tetrahydrate (0.003 moles), sodium bromide (0.005 moles), ethylbenzene (0.027 moles) and hydrogen peroxide (35%, 0.22 moles) were used. The final reaction mixture, analysed by HPLC, revealed that 97.0% of the ethylbenzene had been consumed, yielding products including acetophenone (91.1% yield).

EXAMPLE IV

The procedure of Example III was repeated, but this time cumene (0.056 moles) and hydrogen peroxide (35%, 0.22 moles) were used. The reaction mixture, analysed by HPLC, revealed that 87.4% of the cumene had been consumed, yielding products including acetophenone (43.1% yield) and 2-phenyl-2-propanol (30.6% yield).

EXAMPLE V

The procedure of Example I was repeated, but this time cobalt (II) acetate tetrahydrate (0.008 moles), sodium bromide (0.04 moles), diphenylmethane (0.055 moles) and hydrogen peroxide (35%, 0.28 moles) were used. The final reaction mixture, analysed by HPLC, revealed that 91.5% of the diphenylmethane had been consumed, yielding products including benzophenone (72.3% yield).

EXAMPLE VI

The procedure of Example I was repeated, but this time cobalt (II) acetate tetrahydrate (0.012 moles), sodium bromide (0.05 moles), dichlorotoluene (0.074 moles), acetic acid (100 g) and hydrogen peroxide (70%, 0.68 moles) were used and the reaction was performed at 90° C. for three hours. The final reaction mixture, analysed by HPLC, revealed that 66.0% of the dichlorotoluene had been consumed, yielding products including dichlorobenzaldehyde (15.2% yield) and dichlorobenzoic acid (23.8% yield).

EXAMPLE VII

This example demonstrates the oxidation of dichlorotoluene by the prior art process described in U.S. Pat. No. 3,969,405.

The procedure of Example VI was repeated, but this time no hydrogen peroxide was used. Instead, molecular oxygen (air) was bubbled through the reaction mixture for sixteen hours. The final reaction mixture, analysed by HPLC, revealed that none of the dichlorotoluene had undergone oxidation.

A comparison of the results from Example VI with the results from Example VII demonstrates the superior performance of the process of the present invention over the process of the prior art.

EXAMPLE VIII

The procedure of Example I was repeated, but this time cobalt (II) acetate tetrahydrate (0.008 moles), sodium bromide (0.001 moles), toluene (0.056 moles) and hydrogen peroxide (35%, 0.21 moles) were used and the reaction carried out at 44° C. for three hours in total under a nitrogen atmosphere. The final reaction mixture, analysed by HPLC, revealed that 46.8% of the toluene had been consumed, yielding products including benzaldehyde (29.7% yield). No benzoic acid was detected, illustrating that the process can be controlled to give oxidation to aldehydes in preference to acids.

EXAMPLE IX

The procedure of Example I was repeated, but this time cobalt (II) bromide (0.005 moles) (instead of cobalt (II) acetate tetrahydrate and sodium bromide) and hydrogen peroxide (40%, 0.22 moles) and the reaction was performed at 60° C. for a total of 3.5 hours. The final reaction mixture, analysed by HPLC, revealed that 70.2% of the toluene had been consumed, yielding products including benzaldehyde (27.2% yield) and benzoic acid (41.7% yield). This example demonstrates the suitability of cobalt (II) bromide as a source of cobalt (II) ions and bromide ions.

EXAMPLE X

The procedure of Example I was repeated, but this time Cobalt (II) acetate tetrahydrate (0.5 g, 0,002 moles), bromine (0.5 g, 0,003 moles), toluene (2.58 g, 0.028 moles), acetic acid (25 g) and hydrogen peroxide (35%, 0.22 moles) were used. The total reaction time was 3 hours. The analysis of the reaction mixture revealed that 79.2% of the toluene had been consumed, yielding products including benzylalcohol (6.6% yield), benzaldehyde (31.54% yield) and benzoic acid (25.18% yield).

EXAMPLE XI

This example demonstrates the selective oxidation of p-xylene by the process of the present invention.

Cobalt (II) acetate tetrahydrate (0.5 g, 0,002 moles), sodium bromide (0.005 moles), p-xylene (0.027 moles) and 25 g acetic acid were charged to a vessel fitted with a condenser, overhead paddle stirrer and thermometer and heated to 80° C. Hydrogen peroxide (40%, 0.22 moles) was added dropwise over 40 minutes down the condenser. During this time the reaction mixture changes from a deep blue colour to pink. The reaction was continued for a further 80 minutes when the reaction was stopped and the reaction mixture analysed by HPLC. The analysis revealed that 84.8% of the toluene had been consumed, yielding products including tolualdehyde (44.9% yield) and toluic acid (12.6% yield). The reaction mixture contained substantially no polyoxidised products such as terephthalic acid.

EXAMPLE XII

This example illustrates the selective oxidation of mesitylene by the process of the present invention.

Cobalt (II) acetate tetrahydrate (0.5 g, 0.002 moles), sodium bromide (1.5 g, 0.015 moles), mesitylene (0.083 moles) and acetic acid (40 g) were charged to a vessel fitted with a condenser, overhead paddle stirrer and thermometer and heated to 80° C. Hydrogen peroxide (50%, 11.5g 100% equivalent; 0.34 moles) was added dropwise over a period of 40 minutes down the condenser. During this period, it was noted that the reaction mixture changed from a deep blue colour to pink. The reaction was continued for a further 80 minutes when it was stopped and the reaction mixture analysed by GC. The analysis showed that 92.4% of the mesitylene had been converted to oxidised products. The oxidised products included 3,5-dimethyl benzaldehyde (31.4% yield) and 3,5-dimethyl benzoic acid (35.4% yield). Substantially no polyoxidised products were found in the reaction mixture.

EXAMPLE XIII

Cobalt (II) acetate tetrahydrate (0.5 g, 0.002 moles), sodium bromide (0.5 g, 0.005 moles), benzyl alcohol (2.93 g, 0.027 moles) and acetic acid (25 g) were charged to a vessel fitted with a overhead paddle stirrer, thermometer and condenser and heated to 80° C. Hydrogen peroxide (30%, 0.22 moles) was added dropwise down the condenser over two hours during which time the reaction mixture changed colour from deep blue to pink. The reaction was continued for a further 90 minutes after which it was stopped and analysed by HPLC. The analysis revealed that 99.0% of the benzyl alcohol had been consumed, yielding products including benzaldehyde (50.2% yield) and benzoic acid (48.8% yield).

EXAMPLE XIV

The procedure of Example XIV was repeated, but this time benzaldehyde (2.88 g, 0.027 moles) was used. The reaction mixture, analysed by HPLC, showed that 84.7% of the benzaldehyde had been consumed, yielding products including benzoic acid (81.7% yield).

EXAMPLE XV

This example illustrates the use of forcing conditions which achieve less selective poly oxidation.

Cobalt (II) acetate tetrahydrate (0.6g, 0.0024 moles), sodium bromide (1.7g, 0.017 moles), 1,2,3-trimethylbenzene (10 g, 0.083 moles) and acetic acid (47 g) were charged to a vessel fitted with a condenser, overhead paddle stirrer and thermometer and heated to 100° C. Hydrogen peroxide (70%, 16.1 g 100% equivalent; 0.47 moles) was added dropwise over a period of 80 minutes down the condenser. The reaction was continued for a further 80 minutes when it was stopped and the reaction mixture analysed by GC. The analysis showed that the products comprised methyl-2,3-benzenedicarboxaldehyde, methyl-2,6-benzenedicarboxaldehyde, 2,3-dimethylbenzoic acid and 2,6-dimethylbenzoic acid. As estimated from GC peak areas, the two acids comprised approximately 70% of the product, the two aldehydes comprising approximately 30% of the product.

We claim:

1. A process for oxidising an alkylaromatic compound comprising reacting said alkylaromatic compound with an oxidising system in the presence of a protic solvent selected from the group consisting of carboxylic acids having one to five carbon atoms, said alkylaromatic compound having at least one alkyl substituent which is not tertiary at the carbon positioned alpha to the aromatic ring, said oxidising system comprising at least 0.01 moles of cobalt (III) ions per mole of alkylaromatic compound, at least 0.01 moles of bromide ions per mole of alkylaromatic compound, and more than 0.5 mole of hydrogen peroxide per mole of alkylaromatic compound.

2. A process as claimed in claim 1, wherein an alkyl substituent of the alkylaromatic compound has at least one hydrogen atom at the alpha position relative to the aromatic ring.

3. A process as claimed in claim 1 or claim 2, wherein the alkylaromatic compound comprises a poly(alkyl)aromatic compound.

4. A process as claimed in claim 3, wherein said alkylaromatic compound has a plurality of identical alkyl substituents.

5. A process as claimed in claim 3, wherein the cobalt (III) ions are present in an amount of from 0.03 to 0.1 moles per mole of poly(alkyl)aromatic compound.

6. A process as claimed in claim 3, wherein the bromide ions are present in an amount of from 0.04 to 0.15 moles per mole of poly(alkyl)aromatic compound.

7. A process as claimed in claim 3, wherein the protic solvent is present in an amount of 3 to 12 times the weight of the poly(alkyl)aromatic compound.

8. A process as claimed in claim 3, wherein the cobalt (III) ions are present in an amount of from 0.03 to 0.1 moles per mole of poly(alkyl)aromatic compound, and the bromide ions are present in an amount of from 0.04 to 0.15 moles per mole of poly(alkyl)aromatic compound.

9. A process as claimed in claim 8, wherein the protic solvent is present in an amount of 4 to 10 times the weight of the poly(alkyl)aromatic compound.

10. A process as claimed in claim 3, wherein the hydrogen peroxide is present in an amount of from 4 to 8 moles per mole of poly(alkyl)aromatic compound.

11. A process as claimed in claim 1 or claim 2, wherein the alkylaromatic compound comprises a monoalkylaromatic compound.

12. A process as claimed in claim 11, wherein the cobalt (III) ions are present in an amount of from 0.02 to 0.12 moles per mole of monoalkylaromatic compound.

13. A process as claimed in claim 12, wherein the cobalt (III) ions are present in an amount of from 0.06 to 0.12 moles per mole of monoalkylaromatic compound.

14. A process as claimed in claim 11, wherein the bromide ions are present in an amount of from 0.02 to 0.2 moles per mole of monoalkylaromatic compound.

15. A process as claimed in claim 14, wherein the bromide ions are present in an amount of from 0.06 to 0.16 moles per mole of monoalkylaromatic compound.

16. A process as claimed in claim 11, wherein the protic solvent is present in an amount of from 3 to 15 times the weight of monoalkylaromatic compound.

17. A process as claimed in claim 11, wherein the cobalt (III) ions are present in an amount of from 0.02 to 0.12 moles per mole of monoalkylaromatic compound and the bromide ions are present in an amount of from 0.02 to 0.2 moles per mole of monoalkylaromatic compound.

18. A process for oxidising a monoalkylaromatic compound comprising reacting said monoalkylaromatic compound with an oxidising system in the presence of a protic solvent selected from the group consisting of carboxylic acids having from one to five carbon atoms, said monoalkylaromatic compound having an alkyl substituent which is not tertiary at the carbon positioned alpha to the aromatic ring, said oxidising system comprising 0.02 to 0.12 moles of cobalt (III) ions per mole of monoalkylaromatic compound, 0.02 to 0.2 moles of bromide ions per mole of monoalkylaromatic compound and more than 0.5 mole of hydrogen peroxide per mole of monoalkylaromatic compound.

19. A process as claimed in claim 18, wherein the cobalt (III) ions are present in an amount of from 0.06 to 0.12 moles per mole of monoalkylaromatic compound.

20. A process as claimed in claim 18, wherein the bromide ions are present in an amount of from 0.06 to 0.12 moles per mole of monoalkylaromatic compound.

21. A process as claimed in claim 18, wherein the protic solvent is present in an amount of from 8 to 12 times the weight of monoalkylaromatic compound.

22. A process as claimed in claim 11, wherein the hydrogen peroxide is present in an amount of from 3 to 10 moles per mole of monoalkylaromatic compound.

23. A process as claimed in claim 22, wherein the hydrogen peroxide is present in an amount of from 4 to 8 moles per mole of monoalkylaromatic compound.

24. A process as claimed in any one of claims 1, 2, or 18–21, wherein an alkyl substituent of the alkylaromatic compound is a ($C_1$–$C_6$) alkyl substituent.

25. A process as claimed in claim 24, wherein an alkyl substituent of the alkylaromatic compound is a methyl substituent.

26. A process as claimed in any one of claims 1, 2, or 18–21, wherein an alkyl substituent of the alkylaromatic compound is substituted with at least one phenyl-, hydroxy-, halo or oxy-substituent.

27. A process as claimed in claim 24, wherein the aromatic substituent of the alkylaromatic compound is substituted with at least one fluoro, chloro, bromo, iodo, nitro or oxygenated substituent.

28. A process as claimed in any one of claims 1, 2, or 18–21, wherein the cobalt (III) ions are formed in-situ by the oxidation of cobalt (II) ions sourced from a cobalt (II) salt selected from the group consisting of cobalt (II) acetate, cobalt (II) propionate, cobalt (II) naphthenate and cobalt (II) bromide.

29. A process as claimed in any one of claims 1, 2, or 18–21, wherein the bromide ions are sourced from bromide or a bromide salt selected from the group consisting of hydrogen bromide, ammonium bromide, cobalt (II) bromide, sodium bromide and potassium bromide.

30. A process as claimed in any one of claims 1, 2, or 18–21, wherein the process is effected at a temperature of at least 40° C.

31. A process as claimed in claim 8, wherein the process is effected at a temperature of at least 60° C.

32. A process as claimed in any one of claims 1, 2, or 18–21, wherein the process employs forcing conditions comprising a combination of a temperature in the range of from 80° C. to 100° C. and to use of a hydrogen peroxide solution comprising greater than 65% $H_2O_2$ by weight.

* * * * *